United States Patent [19]

Kouzai et al.

[11] 4,073,837
[45] Feb. 14, 1978

[54] PROCESS FOR PRODUCING WHOLLY AROMATIC POLYAMIDE FIBERS

[75] Inventors: Keiji Kouzai; Yutaka Tabe; Eiji Masunaga, all of Iwakuni; Kichiro Matsuda, Hino, all of Japan

[73] Assignee: Teitin Limited, Osaka, Japan

[21] Appl. No.: 607,790

[22] Filed: Aug. 26, 1975

Related U.S. Application Data

[63] Continuation of Ser. No. 360,535, May 15, 1973, abandoned.

[30] Foreign Application Priority Data

May 18, 1972 Japan .................................. 47-48521
June 13, 1972 Japan .................................. 47-58264

[51] Int. Cl.$^2$ ............................................. D01F 7/00
[52] U.S. Cl. .................................. 264/38; 264/178 F; 264/179; 264/184; 264/210 F
[58] Field of Search .................. 264/184, 38; 260/78 R

[56] References Cited

U.S. PATENT DOCUMENTS

| | | | |
|---|---|---|---|
| 3,079,219 | 2/1963 | King | 264/184 |
| 3,084,384 | 4/1963 | Denyes et al. | 264/184 |
| 3,086,050 | 4/1963 | Nofarbartolo et al. | 260/561 |
| 3,414,645 | 12/1968 | Morgan | 264/184 |
| 3,532,677 | 10/1970 | Baron | 260/79.3 |
| 3,751,546 | 8/1973 | Horoldt et al. | 264/184 |
| 3,787,372 | 1/1974 | Blocker | 260/78 R |
| 3,944,522 | 3/1976 | Tohyama et al. | 264/184 |

Primary Examiner—Jay H. Woo
Attorney, Agent, or Firm—Sherman & Shalloway

[57] ABSTRACT

A process for producing wholly aromatic polyamide fibers by extruding a spinning solution of a wholly aromatic polyamide in an amide solvent into an aqueous coagulating bath containing inorganic salts, said process comprising feeding an aqueous coagulating liquid containing calcium chloride and having an amide solvent concentration of not more than 3% by weight to the vicinity of a spinneret, flowing the coagulating liquid in said bath at an average velocity not more than 0.1 time the velocity of yarn take-up in the yarn advancing direction, discharging the coagulating liquid having an amide solvent concentration of not less than 4% by weight from said bath, treating the coagulating bath with an organic solvent consisting substantially of methylene chloride, and extracting and recovering the amide solvent from the coagulating liquid.

6 Claims, 3 Drawing Figures

PROCESS FOR PRODUCING WHOLLY AROMATIC POLYAMIDE FIBERS

This is a continuation of application Ser. No. 360,535, filed May. 15, 1973, now abandoned.

This invention relates to a process for preparing wholly aromatic polyamide fibers on a commercial scale. More specifically, the invention relates to a process for preparing wholly aromatic polyamide fibers of excellent quality with good productivity, which comprises extruding a spinning solution containing a wholly aromatic polyamide dissolved in an amidetype solvent into an aqueous coagulating bath containing calcium chloride, with the amide solvent being recovered advantageously.

It has previously been known (for example, by Japanese Patent Publication No. 1555/72) that a wholly aromatic polyamide, especially an N-substituted wholly aromatic polyamide, can be dissolved in an amide solvent such as N-methyl-2-pyrrolidone (to be referred to simply as NMP) to form a spinning solution, and the spinning solution can be extruded into an aqueous coagulating bath containing calcium chloride to form wholly aromatic polyamide fibers.

However, since the solution of a wholly aromatic polyamide in an amide solvent has extremely poor coagulatability as compared with other polymer solutions (for example, a solution of polyacrylonitrile in N,N-dimethyl formamide), fibers can be produced only with poor productivity when it is desired to produce them commercially by the wet spinning method.

When fibers are produced commercially, the recovery of the solvent is essential, but no method has ever been known to recover the amide solvent advantageously from the coagulating liquid discharged from the coagulating bath.

It is therefore an object of this invention to provide a wet spinning method whereby it is possible to produce wholly aromatic polyamide fibers of good quality with high productivity.

Another object of this invention is to provide a process for recovering the amide solvent advantageously from the coagulating liquid discharged from the coagulating bath.

investigations of the inventors with a view to achieving the above objects led to the discovery of the following facts.

(a) The concentration of the amide solvent in the coagulating bath exerts a great effect on the condition of spinning and the quality of the resulting filaments. Especially when the concentration of the amide solvent goes beyond a certain limit in a region where the spinning solution has just been extruded from the spinneret and the coagulation of the filaments proceeds, the spinning condition and the quality of the filaments drastically change.

(b) However, the effect of the NMP concentration on the spinning condition and the yarn quality on that portion of the coagulating bath in which the spun yarn is leaving is relatively small, and no trouble occurs even if the NMP concentration is increased to some extent.

(c) By extracting the coagulating liquid discharged from the coagulating bath with methylene chloride, it is possible to recover the amide solvent efficiently.

(d) Since the recovery efficiency varies greatly according to the concentration of the amide solvent in the discharged coagulating liquid and the specific gravity of the liquid, these conditions should be strictly controlled.

Based on these findings, the inventors furthered their investigations on a commercial scale, and finally arrived at the process of the present invention whereby wholly aromatic polyamide fibers of excellent quality can be prepared in good spinning condition, and the amide solvent can be recovered efficiently and economically.

According to this invention, there is provided a process for producing wholly aromatic polyamide fibers by extruding a spinning solution of a wholly aromatic polyamide in an amide solvent into an aqueous coagulating bath containing inorganic salts, said process comprising feeding an aqueous coagulating liquid containing calcium chloride and having an amide solvent concentration of not more than 3 % by weight to the vicinity of a spinneret, flowing the coagulating liquid in said bath at an average velocity not more than 0.1 time the velocity of yarn take-up in the yarn advancing direction, discharging the coagulating liquid having an amide solvent concentration of not less than 4 % by weight from said bath, treating the coagulating bath with an organic solvent consisting substantially of methylene chloride, and extracting and recovering the amide solvent from the coagulating liquid.

In the specification, the average velocity of the coagulating bath is expressed by 1/100 (m/min.) of the amount (cm³/min.) of the coagulating liquid flowing into the coagulating bath per minute per average sectional area (cm²) of the coagulating bath. The average sectional area of the coagulating bath is the quotient obtained by dividing the volume (cm³) of the coagulating bath by its height (cm).

The "wholly aromatic polyamide", as referred to in the present specification and claims, denotes a synthetic linear polyamide in which at least 85 mol%, preferably at least 90 mol%, of the recurring units are composed of units expressed by formula (1) and/or formula (2) shown below:

$$-NR_1-Ar-NR_2CO-Ar'-CO- \qquad (1)$$

$$-NP_3-Ar-CO- \qquad (2)$$

wherein Ar and Ar' each represent a bifunctional aromatic ring, each of $R_1$, $R_2$ and $R_3$ is a hydrogen atom or methyl group, Ar and Ar' are the same or different, and $R_1$ and $R_2$ are the same or different.

Suitable examples of such a wholly aromatic polyamide are poly(m-phenylene isophthalamide), and copolymers composed principally of said polymer (for example, m-phenylene isophthalamide/terephthalamide copolymer). Those containing at least 75 mole% of m-phenylene isophthalamide units are preferred. Examples of the comonomers are m-phenylene terephthalamide, m-benzamide, m-phenylene isophthalate-isophthalamide, and m-toluylene isophthalamide.

Suitable solvents for the wholly aromatic polyamides are amide compounds such as N-methyl-2-pyrrolidone, N,N'-dimetyl acetamide, N,N'-dimethyl formamide, and hexamethyl phosphoramide, or their mixtures.

The concentration of the wholly aromatic polyamide in the spinning solution is not critical, but is usually from 15 to 30 % by weight, preferably from 18 to 25 % by weight. If desired, the solution may contain a pigment such as titanium oxide or carbon black, a dye, a heat (oxidation) stabilizer or a light stabilizer. Furthermore, it may also contain inorganic salts in order to increase the solubilizing ability of the subject.

As required, the spinning solution is filtered, defoamed and metered, and then fed into the spinneret from which it is extruded into the coagulating bath.

Figure 2:
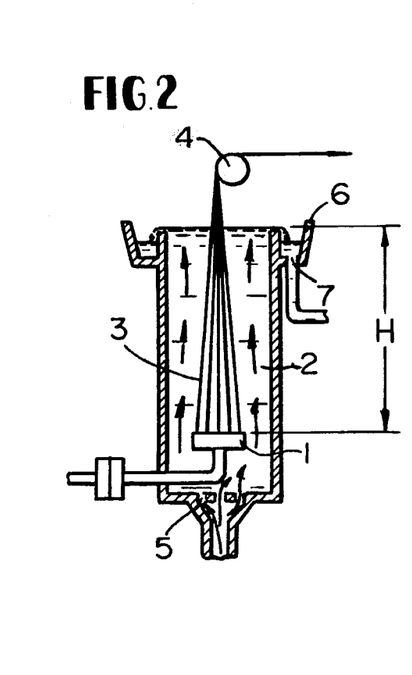
FIG. 2 shows a coagulating bath of the vertical type adapted to flow the coagulating liquid upwardly from below.
Figure 3:
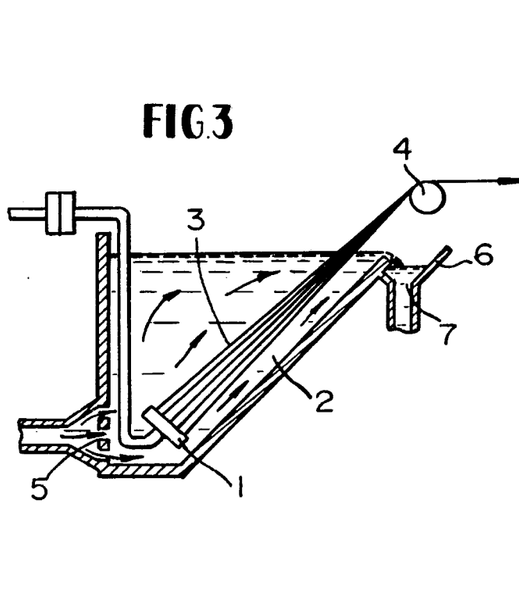
FIG. 3 is a sketch of a coagulating bath of the inclined type adapted to flow the coagulating liquid obliquely upwardly from below.

Suitably, the spinneret has at least 5,000 orifices. Although a spinneret of the doughnut shape which permits the coagulating liquid to flow in its central part is preferred, a disc-like spinneret can also be used. The coagulating bath may be of the vertical type as shown in FIG. 2 of the accompanying drawings in which the spinneret is provided roughly horizontal and the coagulating liquid is caused to flow upwardly from below, or of the inclined type as shown in FIG. 3 in which the spinneret is provided inclinedly, and the coagulating liquid is caused to flow obliquely upwardly from below.

In any case, in the present invention, an aqueous solution containing calcium chloride and having an amide solvent concentration of not more than 3 % by weight is fed into the coagulating bath from one end of the bath (rear and/or side of the spinneret), and caused to flow in the bath in the yarn advancing direction. Then, the coagulating liquid whose solvent concentration has increased as a result of the coagulation of the yarn is discharged from the outer end (the yarn withdrawing side) of the coagulating bath.

By this contrivance, the coagulating liquid of low solvent concentration is always supplied to the vicinity of the spinneret, and therefore, filaments of good quality can be prepared in good spinning condition.

If the concentration of the solvent of the coagulating liquid exceeds 3 % by weight, the spinning condition becomes extremely poor.

The amount of calcium chloride present in the coagulating liquid is at least 35 % by weight, especially from 40 to 45 % by weight. Part of the calcium chloride, preferably not more than 35 % by weight thereof, may be replaced by at least one inorganic salt such as magnesium chloride, calcium nitrate and zinc chloride. In this case the concentration of calcium chloride in the coagulating bath is adjusted to not less than 20 % by weight, and the total concentration of the salts, to at least 35 % by weight, preferably 40 to 45 % by weight. The temperature of the coagulating bath is at least 60° C., especially 80° to 100° C. Therefore, the coagulating liquid to be fed to the coagulating bath is preferably pre-heated to a temperature of about 80° to 100° C.

The average flow velocity of the coagulating liquid in the coagulating bath is not more than 0.1 time the yarn take-up velocity. This velocity is extremely low as compared with the flow velocity of a coagulating liquid for performing spinning stably by an ordinary wet-spinning process (0.5-1.5 times the yarn take-up velocity). It is surprising that stable spinning can be performed at a flow velocity within this range.

If the flow velocity of the coagulating liquid exceeds 0.1 times the yarn take-up speed, the amount of the amide solvent moving into the coagulating liquid per unit weight decreases, and the concentration of the amide solvent present in the discharged coagulating liquid is reduced. This results in an increase in the amount of the liquid being in an extracting and recovering step, and leads to economic disadvantage. Furthermore, the coagulating liquid flow becomes turbulent in the vicinity of the spinneret to cause the agglutinization of the filaments, and good quality fibers cannot be obtained.

The lower limit of the flow velocity of the coagulating liquid is one sufficient to ensure the presence of a fresh coagulating liquid having a solvent concentration of not more than 3 % throughout the spinning operation. In a coagulating bath of the vertical type as described above, a fresh coagulating liquid can always be made present in the vicinity of the spinneret if the flow velocity of the coagulating liquid is at least 0.04 times the yarn take-up speed.

The coagulating liquid discharged from the coagulating bath is then extracted with methylene chloride to recover the amide solvent. It is necessary that at this time, the concentration of the amide solvent in the coagulating liquid discharged from the coagulating bath be at least 4 % by weight, preferably at least 5 % by weight. If the concentration of the amide solvent is less than 4 % by weight, the amount of the treating liquid in the extracting and recovering step increases, and the solvent cannot be recovered advantageously.

Preferably, the coagulating liquid is discharged when it has a specific gravity of at least 1.36 as measured at 60° C. By this contrivance, the methylene chloride layer and the coagulating liquid layer can be easily separated from each other by the difference in specific gravity (the specific gravity of methylene chloride at 60° C. is 1.33), and the extraction can be continuously performed by the countercurrent extracting process. However, even if the specific gravity of the discharged coagulating liquid is less than 1.36, the amide solvent can be extracted and recovered by mixing the coagulating liquid sufficiently and then allowing the mixture to stand.

Preferably, methylene chloride is used in this extracting process in an amount of 0.8 to 2.0 times, preferably 1.0 to 1.5 times, the weight of the discharged coagulating liquid. If the extraction efficiency is adjusted to at least 60 %, preferably at least 75 %, the above-mentioned conditions can be met when the coagulating liquid after extraction is recycled to the coagulating bath, and the stable operation of the extracting and recovering step can be effected.

The coagulating liquid from which a part or whole of the amide solvent has been removed by extraction with methylene chloride is recycled to the coagulating bath either as such or after the concentration of the amide solvent or calcium chloride has been controlled.

The amide solvent in the methylene chloride layer is recovered by evaporation and distillation, and is used again in the preparation of the spinning solution.

Methylene chloride used for the extracting process may contain another organic solvent having a specific gravity of not more than 1.3 and being soluble in methylene chloride and the amide solvent and being insoluble in water, such as 1,2-dichloroethane, toluene, xylene or benzene, but preferably the amount of methylene chloride is at least 85 %.

On the other hand, the spinning solution which has been extruded is withdrawn upwardly while solidifying in the coagulating bath, and then led to a washing step.

Preferably, the velocity of taking up the filaments from the coagulating bath is adjusted to 1-5 m/min. If the take-up velocity is within the above-defined range, the coagulation is performed more uniformly, and filaments free from breakage or coagulating unevenness can be obtained with high productivity.

If the distance (H) between the spinneret face and the upper surface of the coagulating bath is adjusted within the range expressed by the following equation, the spinning condition becomes very stable:

$$150 \geq H \geq (2D + 5) + 1.5S$$

wherein $D$ is the denier size of a single filament of the final fiber obtained by drawing and heat-treatment, which is within the range of 1 to 30 denier, and $S$ is the velocity (m/min.) of taking up filaments from the coagulating bath, which is within the range of 1 to 5 meters/min.

If the distance H is smaller than the lower limit defined above, the filaments may sometimes lose their transparency. Furthermore, the single filaments may adhere to one another, and filament-breakage or the formation of fuzzes occurs. If the distance H is larger than 150 cm, it becomes somewhat difficult to withdraw the filaments at the beginning of spinning.

The filaments which have been taken up after coagulation are washed with water to remove calcium chloride entrained in the coagulation bath and the solvent remaining in the filaments. Then, the filaments are drawn at a prescribed draw ratio (preferably 2 to 4 X) in a warm water bath and/or a vapor bath, and heat-treated at least 280° C. while being under a restricted shrinkage, constant length or stretch (preferably 5 to 100 % stretched state) to form highly oriented and crystallized wholly aromatic polyamide fibers.

The invention will further be described by reference to the accompanying drawings in which.

Figure 1:
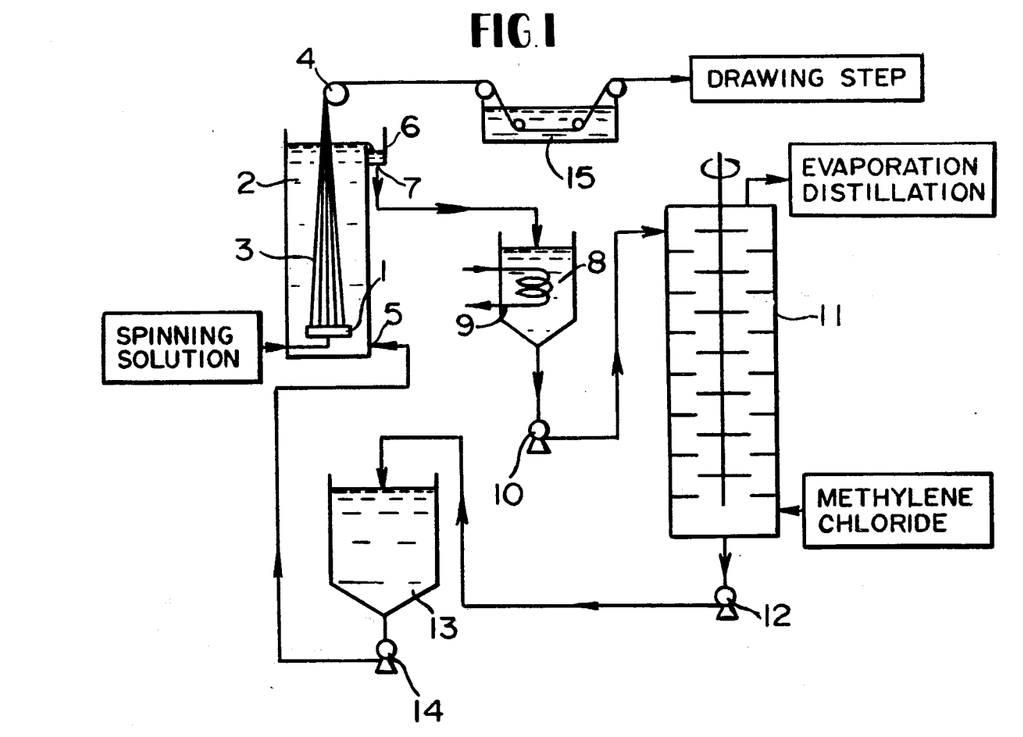
FIG. 1 is a flow diagram showing the performance of one embodiment of the present invention.

In FIGS. 1 to 3, the reference numeral 1 represents a spinneret; 2, a coagulating bath; 3, filaments; 4, a take-up roller; 5, a feed inlet for the coagulating liquid; 6, a trough for receiving the coagulating liquid that has overflowed; 7, a coagulating liquid exhaust port; 8 and 13, a reservoir; 9, a cooling coil; 10, 12 and 14, a pump; 11, an extraction tower; and 15, a water washing bath.

A spinning solution obtained by dissolving a wholly aromatic polyamide in an amide solvent is extruded into the coagulating bath through the spinneret 1. The coagulated filaments 3 are taken up at a certain take-up velocity by the take-up roller 4, washed with water in the water bath 15, and then fed to the subsequent drawing step.

On the other hand, the coagulating liquid is fed from the feed inlet 5 rearward of the spinneret, and flows within the coagulating bath 2 in the direction shown by arrows in FIGS. 2 and 3. It is then caused to overflow from the yarn take-up side of the coagulating bath and is received on the trough 6, and thence the coagulating liquid is led into the reservoir 8 through the exhaust port 7. It is cooled to about 50° C. by the cooling coil 9 through which water flows, and supplied to the upper part of the extracting tower 11 by the pump 10. Methylene chloride is fed into the lower part of the extracting tower, and within this tower, the amide solvent is the coagulating liquid is extracted and transferred into the methylene chloride. The coagulating liquid after extraction is taken out by the pump 12 from the bottom of the extraction cell, and received by the reservoir 13, from which the coagulating liquid is supplied to the coagulating bath by the pump 14.

On the other hand, the methylene chloride containing the amide solvent is taken out from the upper part of the extraction tower, and led to an evaporation device where the methylene chloride is evaporated and separated from the amide solvent. The amide solvent is further distilled under reduced pressure to purify and recover it. The amide solvent is reused for the preparation of the spinning solution, and methylene chloride is reused as an extracting agent.

According to the present invention which has been described above, wholly aromatic polyamide fibers can be produced in very good spinning condition, and the formation of agglutinized filaments or abnormal filaments is reduced. Furthermore, the solvent can be recovered economically and efficiently. The present invention makes it possible to produce filaments in various denier sizes, from fine to heavy denier, and heavy denier yarns for industrial use can also be produced.

The invention will be described in greater detail by the following Examples. The various properties shown there were measured in accordance with the following methods.

(1) Rate of Tenacity Fluctuation

This shows the extent of the dispersion in the measured values of a single filament tenacity, and is determined by the following equation.

Rate of tenacity fluctuation =

$$\frac{\text{Dispersion } [\sigma] \text{ of single filament tenacity}}{\text{Average value } [\bar{x}] \text{ of the single filament tenacity}} \times 100(\%)$$

The tenacity of the single filament was measured with respect to 20 samples.

(2) Amount of abnormal fibers 50 gr. of raw staples were spread by hand, and foreign matters such as dope scum, undrawn filaments or agglutinized filaments were taken out and their weight was measured. The amount obtained is expressed by % by weight (3) Number of crimps A monofilament sample was adhered to a sheet (space distance 25 mm, ]-shaped) by means of an adhesive. It was then mounted on a torsion-type or chain-type crimp tester, and an initial load of 2 mg per denier was exerted on the filament, and the number of crimps per mm of the sample was read. The number obtained was converted to that per 25 mm.

(4) Degree of crimping

The sample used to measure the number of crimps was placed under a load of 50 mg per denier for 30 seconds to stretch out the crimps of the sample, and the length $b$ (mm) of the sample under the load was measured. The degree of crimping was calculated in accordance with the following equation:

$$\text{Degree of crimping}(\%) = \frac{b - a}{b} \times 100$$

wherein $a$ is the length of the sample when the initial load is 2 mg/denier, and $b$ is the length of the sample when the load is 50 mg/denier.

(5) Degree of crimp elasticity and Degree of residual crimp

After reading the length of the sample under the heavy load in the measurement of the degree of crimping, all the load was removed, and the sample was allowed to stand for 2 minutes. Again, a load of 2 mg/denier (the same as the initial load) was exerted on the sample, and the length $c$ (mm) of the sample at this time was measured. These properties were calculated in accordance with the following equations.

$$\text{Degree of crimp elasticity} = \frac{b-c}{b-a} \times 100$$

$$\text{Degree of residual crimp} = \frac{b-c}{b} \times 100$$

Example 1

20.5 parts of a wholly aromatic polyamide having an inherent viscosity of 1.9 and obtained by copolymerization of m-phenylene diamine, isophthaloyl chloride and terephthaloyl chloride (copolymerization mole ratio 98 : 2) was dissolved in 79.5 parts of N-methyl-2-pyrrolidone, and the solution was defoamed to prepare a spinning solution held at 70° C. The solution was extruded at a rate of 234 cc/min. into a coagulating bath through a spinneret having 6,000 holes each with a diameter of 0.12 mm secured to the bottom of the coagulating bath substantially horizontal thereto as shown in FIG. 2. It was coagulated in the filament form in the coagulating bath, and then taken up at a rate of 2.1 meters/min The coagulating bath contained a coagulating liquid held at 95° C. and consisting of an aqueous solution containing N-methyl-2-pyrrolidone in a concentration of 1.7 % and calcium chloride in a concentration of 42 %. The coagulating liquid was followed to flow in the coagulating bath at an average velocity of 0.17 meter/min. (the yarn take-up velocity multiplied by 0.08), and the coagulating liquid having an n-methyl-2-pyrrolidone concentration of 6.2 % and a specific gravity at 60° C. of 1.375–1.380 was discharged from the upper part of the coagulating bath.

The filaments which had been taken up from the coagulating liquid were washed thoroughly with water to remove the solvent, drawn to 2.75 times the original length in boiling water held at 95° C., dried, drawn to 1.4 times on a hot plate held at 310° C., then heat-treated. The filaments were then crimped using a stuffer crimper, and the crimped tow was cut to a fiber length of 76 mm to form stable fibers.

The spinning and drawing conditions were good, and there was no such trouble as the agglutinization, opacification or breaking of the filaments. The number of wrapping during the spinning process and the properties of the fibers obtained were as follows:

| Number of wrapping | 0–0.01 time/hour |
| Denier size | 9.97 denier |
| Tenacity | 4.95 g/d |
| Elongation | 45 % |
| Rate of tenacity fluctuation | 9.1 % |
| Amount of abnormal fibers | $1 \times 10^{-4}$ % by weight |

On the other hand, the coagulating liquid which was taken out from the coagulating bath was supplied to the reservoir as shown in FIG. 1, and after its temperature was adjusted to 50° C., it was fed to an extraction tower where it was treated with 1.3 times its volume of methylene chloride to extract and recover the N-methyl-2-pyrrolidone present in the coagulating liquid. By this treatment, a calcium chloride aqueous solution having an N-methyl-2-pyrrolidone concentration of 1.7 % was continuously taken out from the extraction tower, and recycled to the coagulating bath.

COMPARATIVE EXAMPLE 1

Example 1 was repeated except that the amount of the coagulating liquid fed was decreased, and the average velocity of the coagulating liquid was adjusted to 0.03 times the yarn take-up velocity. The concentration of N-methyl-2-pyrrolidone in the coagulating liquid to be fed to the coagulating bath gradually increased, and the spinnability of the spinning solution became poor. At the same time, the N-methyl-2-pyrrolidone concentration of the coagulating liquid increased and the specific gravity of the coagulating liquid decreased to below 1.35. Finally, it became impossible to extract and recover N-methyl-2-pyrrolidone using methylene chloride in a countercurrent extracting tower.

COMPARATIVE EXAMPLE 2

Example 1 was repeated except that the amount of the coagulating liquid fed was increased, and the average flow velocity of the coagulating liquid was adjusted to 0.15 times the yarn take-up velocity. The N-methyl-2-pyrrolidone concentration of the calcium chloride aqueous solution fed into the coagulating bath became 1 %, and the NMP concentration of the discharged liquid was 3.5 %.

The liquid flow in the vicinity of the discharged filaments became very much turbulent, and the filaments obtained contained many fine filaments, with the result that wrapping in the spinning process increased. Furthermore, the amount of the liquid to be treated in the extracting step increased, and it was economical.

The filaments obtained had the following properties.

| Denier size | 9.9 denier |
| Tenacity | 4.4 g/denier |
| Elongation | 41 % |
| Rate of tenacity fluctuation | 21 % |
| Amount of abnormal filaments | $650 \times 10^{-4}$ % by weight |

COMPARATIVE EXAMPLE 3

Example 1 was repeated except that an extraction tower of low extracting efficiency was used. The NMP concentration of the calcium chloride aqueous solution to be fed into the coagulating bath was 4.1 %, and the NMP concentraion in the coagulating liquid to be discharged from the coagulating bath was 8.5 %. An equilibrium condition was reached at a specific gravity of 1.36. Spinning was performed. However, there was frequent filament breakage and wrapping in the spinning step, and it was impossible to perform spinning stably. The properties of the filaments were as follows:

| Wrapping in the spinning process | 5 times/hour |
| Denier size | 9.91 denier |
| Tenacity | 4.71 g/de |
| Elongation | 42.1 % |

-continued

| Amount of the abnormal fibers | $340 \times 10^{-4}$ % by weight |
|---|---|

EXAMPLE 2

Poly(meta-phenylene isophthalamide) having an inherent viscosity of 1.90 (20.5 parts) was dissolved in 79.5 parts of N-methyl-2-pyrrolidone, and the solution was defoamed to prepare a spinning solution held at 70° C. As shown in FIG. 2, the spinning solution was fed at a rate of 316 cc/min. into a doughnut type spinneret having 34000 holes each with a diameter of 0.07 mm, which was fitted to the bottom of the bath substantially horizontal, and extruded into a coagulating liquid containing 43 % by weight of calcium chloride. The filaments were coagulated there and taken up at a rate of 2.5 m per minute.

The coagulating liquid was fed to the vicinity of the spinneret from the bottom of the coagulating bath, same as in Example 1, and caused to flow upwardly at an average velocity of 0.20 m/min. Then, it was discharged from the upper part of the coagulating bath. A part of whole of the discharged coagulating liquid was fed into a countercurrent type extraction tower, and treated with methylene chloride to extract the solvent. Then, the coagulating liquid was heated to 95° C., and the NMP concentration was adjusted to various values, whereupon it was recycled to the coagulating bath, and spinning was continued.

The coagulated filaments were sufficiently washed with water as in Example 1, drawn to 2.73 times the original length in a warm water bath held at 95° C., dried, and then drawn to 1.43 times on a hot plate held at 340° C. After crimping, the filaments were cut to a fiber length of 38 mm to form staple fibers.

There was the following relation between the NMP concentration of the coagulating liquid and the quality of the yarn.

for 20 minutes. The mixture was then allowed to stand to separate the methylene chloride/toluene mixed solution containing NMP. The remaining coagulating liquid was again extracted by similar means, and then extracted in two stages, after which it was recycled to the coagulating bath.

The resulting filaments were treated in the same way as in Example 1 to form staple fibers. The draw ratio was 2.73 in boiling water, and 1.43 on a hot plate. The resulting filaments had a tenacity of 5.2 g/de and an elongation of 38.5 % and exhibited a transparent appearance.

EXAMPLE 4

20.5 parts of a wholly aromatic polyamide having an inherent viscosity of 1.85 and obtained by copolymerizing m-phenylene diamine and isophthaloyl chloride and terephthaloyl chloride (copolymerization ratio 98:2) was dissolved in 70.3 parts of N-methyl-2-pyrrolidone, and 0.2 part of titanium oxide was added. The solution was defoamed to prepare a spinning solution held at 70° C.

The spinning solution was extruded at a rate of 355 cc/min. into a coagulating bath of the vertical type through a doughnut type spinneret having 34,000 holes each with a diameter of 0.07 mm which was secured almost horizontal to the bottom of the coagulating bath. The extrudate was coagulated in the filament form in the coagulating bath, and taken up at a speed of 3.1 meters/min. An aqueous solution of calcium chloride having a calcium chloride concentration of 42 % and being held at 73° C. was fed from the bottom of the coagulating bath in the same way as in Example 1, and caused to flow upward in the coagulating bath at an average velocity of 0.19 meter/min. while being fed to the vicinity of the spinneret. Finally, it was discharged from the upper part of the coagulating bath. The discharged coagulating bath was fed from the upper part of a counter current type extracting tower through a

| NMP concentration of the fed liquid (%) | NMP concentration of the discharged liquid (%) | Specific gravity of the discharged liquid | Method of extraction | Tenacity (g/de) | Elongation (%) | Amount of abnormal fibers (%) | Operability* |
|---|---|---|---|---|---|---|---|
| 1.7 | 6.2 | 1.38 | wholly extracted | 5.07 | 41 | 0 | 0 |
| 3.0 | 7.5 | 1.37 | partly extracted | 5.00 | 39 | $1 \times 10^{-4}$ | 0.05 |
| 5.4 | 9.9 | 1.36 | partly extracted | 4.93 | 39 | $250 \times 10^{-4}$ | 4 |

*operability = number of wrappings onto the first stage draw roller as expressed in turns/hour.

EXAMPLE 3

Using the spinning solution prepared in Example 1 and the spinning bath shown in FIG. 2, the spinning was performed under the following conditions.

| | |
|---|---|
| Coagulating bath | Aqueous solution containing 37.5 % of calcium chloride held at 70° C. |
| Feeding side | NMP concentration 1.5 % |
| Discharge side | NMP concentration 5.8 % |
| Specific gravity 1.345 | |

The liquid discharged from the coagulating bath was adjusted to a temperature of 50° C., and fed into the reservoir. The liquid was then mixed with a solution having a specific gravity at 30° C. of 1.29 and consisting of 90 parts of methylene chloride and 10 parts of toluene reservoir. Methylene chloride was fed from the bottom part of the extracting tower in an amount 1.5 times that of the coagulating liquid, and extraction was carried out by countercurrent stirring.

The coagulating liquid which was taken out from the lower part of the extracting tower was recycled to the bottom of the coagulating bath, and the spinning was continued.

The NMP concentration of the calcium chloride aqueous solution to be fed to the bottom of the coagulating bath was 1.5±0.2 %, and the NMP concentration of the coagulating liquid withdrawn from the coagulating bath was 6.7±0.5 % with the specific gravity at 60° C. being 1.38±0.01.

The filaments which were taken up were thoroughly washed with water to remove the solvent, drawn to 2.2 times the original length in boiling water at 95° C., dried, then drawn to 1.9 times on a hot plate at 310° C., heat-treated, crimped by a stuffer crimper, and cut to a fiber length of 51 mm to form staple fibers.

The spinning was performed in good condition, and there was no such trouble as yarn breakage, and the filaments obtained had the following properties.

| | |
|---|---|
| Denier size | 1.78 denier |
| Tenacity | 5.03 g/denier |
| Elongation | 43.8 % |
| Rate of tenacity fluctuation | 8.6 % |
| Number of crimps | 13 per inch |
| Degree of crimping (apparent) | 18 % |
| Degree of residual crimp | 12.5 % |

EXAMPLE 5

22 parts of the polymer used in Example 4 was dissolved in 78 parts of NMP, and the solution was defoamed to prepare a spinning solution held at 70° C.

While being kept at 70° C., the spinning solution was extruded at a rate of 353 cc/min. into a coagulating bath of the inclined type as shown in FIG. 3 through a spinneret having 6000 holes each with a diameter of 0.12 mm which was fitted at an angle of 40° with respect to the horizontal plane. The coagulated filaments were taken up at a rate of 2.1 meters/min.

An aqueous calcium chloride solution having a calcium chloride concentration of 42 % and being held at a temperature of 95° C. was fed into the vicinity of the spinneret from the bottom of the coagulating bath, and caused to flow within the coagulating bath at an average velocity of 0.07 meters/min. It was then discharged from the yarn take-up outlet at the upper part of the coagulating bath.

The discharging coagulating liquid flowed through a reservoir, and subjected to an extraction treatment by the counter current extracting tower method using methylene chloride under the same conditions as in Example 4, and recycled to the coagulating bath to continued the spinning.

The aqueous calcium chloride solution to be fed into the bottom of the coagulating bath had an NMP concentration of 1.7 ± 0.2, and the coagulating liquid taken out from the coagulating bath had an NMP concentration of 6.5 ± 2 % and a specific gravity at 60° C. of 1.37 – 1.38. The filaments obtained were drawn and crimped in the same way as in Example 1 to form staple fibers having a denier size of 15.5 denier, a tenacity of 4.8 g/denier, and an elongation of 45.0 %.

EXAMPLE 6

18 parts of poly(m-phenylene isophthalamide) having an inherent viscosity of 2.2 was dissolved in 82 parts of NMP. The spinning solution obtained which was maintained at 70° C. was extruded at a rate of 16 cc/min. into a coagulating bath of the inclined type as used in Example 5 through a spinneret having 720 holes each with a diameter of 0.08 mm which was secured at an angle of 50° with respect to the horizontal surface. The coagulated filaments were taken up at a take-up velocity of 10 meters/min.

An aqueous solution maintained at 95° C. and containing 25 % of calcium chloride and 18 % of zinc chloride was fed into the vicinity of the spinneret from the bottom of the coagulating bath, and caused to flow in the coagulating bath at an average velocity of 0.2 mm/min. It was discharged from the yarn take-up outlet at the upper part of the coagulating bath.

The coagulating liquid which was thus discharged was caused to flow through a reservoir, and extracted with methylene chloride under the same conditions as in Example 4, and then recycled to the coagulating bath. The inorganic salt solution fed from the bottom of the coagulating bath had an NMP concentration of 2 ± 0.5 %, and the inorganic salt solution discharged from the coagulating bath had an NMP concentration of 7 ± 1 % and a specific gravity at 60° C. of 1.38 to 1.39.

The resulting filaments were washed with water, drawn to 3.2 times the original length in warm water held at 95° C., dried, drawn to 1.43 times on a hot plate at 330° C., and wound up at a rate of 42.5 meters/min. The filament yarn obtained had the following properties.

| | |
|---|---|
| Denier size | 1650 |
| Number of the filaments | 720 |
| Tenacity | 7.5 g/de |
| Elongation | 21 % |
| Initial Young's modulus | 121 g/de |

EXAMPLE 7

The spinning solution as used in Example 4 was extruded at a rate of 241 cc/min. into a spinning bath of the type shown in FIG. 2 having a different height from the spinneret face to the top of the bath, through a doughnut type spinneret having 34000 holes each with a diameter of 0.07 mm. The coagulated filaments were taken up at a rate of 2.1 m/min., washed with water, drawn, and crimped under the same conditions as in Example 4 to form staple fibers.

As will be shown below, when the height was 50 cm and 85 cm, good quality filaments could be obtained, but when it was 20 cm there was the breakage and agglutinization of the filaments, and the amount of abnormal fibers increased. It was therefore difficult to obtain staple fibers of good quality.

| Height from the spinneret face to the top of the coagulating bath (cm) | Tenacity (g/de) | Elongation (%) | Amount of abnormal fibers (%) | Rate of tenacity fluctuation (%) |
|---|---|---|---|---|
| 85 | 5.11 | 42.0 | 0 | 8.4 |
| 50 | 5.03 | 43.8 | 0 | 8.6 |
| 20 | 4.25 | 37 | $760 \times 10^{-4}$ | 21 |

In every case, the coagulating liquid fed into the coagulating bath was a 42 % aqueous solution of calcium chloride and had an NMP concentration of 1.7 ± 0.2 %. The coagulating liquid discharged had an NMP concentration of 6.5 ± 0.5 % and a specific gravity at 60° C. of 1.38 ± 0.01.

The discharged coagulating liquid was treated with methylene chloride in the same way as in Example 4, and recycled to the coagulating bath.

EXAMPLE 8

20.5 parts of a wholly aromatic polyamide having an inherent viscosity of 1.9 and obtained from m-phenylene diamine, isophthaloyl chloride and terephthaloyl chloride (copolymerization ratio 97 : 3) was dissolved in 79.5 parts of N-methyl-2-pyrrolidone, and the solution was defoamed. While being maintained at 70° C., the spinning solution was extruded into a 41 % by weight aqueous solution of calcium chloride maintained at 73° C. through a spinneret having 34,000 holes each with a diameter of 0.07 mm. The coagulating bath used was of the type shown in FIG. 2 in which the distance between the spinneret face to the top of the coagulating bath was 100 cm. The spinning was performed while varying the amount of the polymer extruded and the take-up velocity.

The average velocity of the calcium chloride aqueous solution in the coagulating bath was adjusted to 0.08 times the yarn take-up velocity. The NMP concentration of the calcium chloride aqueous solution was adjusted to 1.5 ± 0.2 %, and the NMP concentration of the coagulating liquid which was discharged from the coagulating bath was adjusted to 6.5 ± 0.5 % (specific gravity at 60° C. being 1.365–1.37). The discharged coagulating liquid was treated with methylene chloride in the same way as in Example 4, and recycled.

The coagulated filaments were washed with water, drawn, crimped and made into staple fibers in the same way as in Example 4. There was the following relation between the yarn take-up speed and the quality of the yarn. When the yarn take-up speed was 7 m/min., there was marked loss of transparency, and only fibers of unsatisfactory quality could be obtained.

| Yarn take-up speed (m/min.) | Denier size (denier) | Tenacity (g/de) | Elongation (%) | Outer appearance |
| --- | --- | --- | --- | --- |
| 2.1 | 1.92 | 5.4 | 41 | Transpatent |
| 3.5 | 1.95 | 5.2 | 43 | Transparent |
| 6 | 2.01 | 3.5 | 31 | Transparency lost |

EXAMPLE 9

A wholly aromatic polyamide having an inherent viscosity of 1.7 which was prepared from 47 parts of m-phenylene diamine, 87 parts of isophthaloyl chloride and 3 parts of terephthaloyl chloride was dissolved in dimethyl acetamide at room temperature to form a spinning solution having a polymer concentration of 22 %. The spinning solution being kept at room temperature was extruded into a coagulating bath of the vertical type at a rate of 380 cc/min. through a doughnut-shaped spinneret having 34,000 holes each with a diameter of 0.07 mm which was provided at the bottom of the coagulating bath, and while being coagulated in the filament form, was taken up at a rate of 3.0 meters/min.

A coagulating liquid having a specific gravity at 60° C. of 1.366 and containing dimethyl acetamide in a concentration of 1.0 % and calcium chloride in a concentration of 39 % was fed at 60° C. into the coagulating bath from the rear of the spinneret, and caused to flow in the coagulating bath at an average flow velocity of 0.24 m/min. (the yarn take-up velocity × 0.08). The coagulating liquid having a dimethyl acetamide concentration of 4.5 and a specific gravity at 60° C. of 1.350 was discharged from the yarn take-up side of the coagulating bath.

The filaments which were withdrawn from the coagulating bath were washed with water to remove the solvent, drawn to 2.73 times the original length in hot water at 95° C., dried by a hot roller, and then drawn again to 1.45 times on a hot plate held at 320° C.

The spinning and drawing conditions were good, and the filament obtained had a denier size of 2.0 denier, a tenacity of 5.28 g/denier and an elongation of 39.5 %.

On the other hand, the coagulating liquid discharged from the coagulating bath was sent to a reservoir, and its temperature was adjusted to 50° C. Then, the coagulating liquid was fed into a reservoir, where it was mixed with 1.3 times the volume of the coagulating liquid of methylene chloride for 20 minutes with stirring. The mixture was allowed to settle for 2 hours, and then extracted in two stages to separate the coagulating liquid from the methylene chloride layer containing dimethyl acetamide. The methylene chloride layer was evaporated and distilled to separate dimethyl acetamide from methylene chloride. The coagulating liquid so recovered was recycled to the spinning bath.

EXAMPLE 10

Example 9 was repeated except that a coagulating liquid having a specific gravity at 60° of 1.384 and containing calcium chloride in a concentration of 25 % and zinc chloride in a concentration of 14 % was used. The resulting filaments had a denier size of 2.0 denier, a tenacity of 5.42 g/de, and an elongation of 38.4 %.

The coagulating liquid discharged from the coagulating bath had a dimethyl acetamide concentration of 4.5 % and a specific gravity of 1.386. The coagulating liquid was sent to a reservoir and its temperature was adjusted to 50° C. Then, it was fed into an extraction tower, and continuously treated with 1.3 times its volume of methylene chloride to extract and recover dimethyl acetamide in the coagulating bath.

By this treatment, a mixed aqueous solution of calcium chloride and zinc chloride which had a dimethyl acetamide concentration of 1.0 % was continously withdrawn, and recycled to the coagulating bath.

EXAMPLE 11

A wholly aromatic polyamide having an inherent viscosity of 1.9 and obtained from 47 parts of m-phenylene diamine, 87 parts of isophthaloyl chloride and 3 parts of terephthaloyl chloride was dissolved in N-methyl-2-pyrrolidone to form a spinning solution having a polymer concentration of 20.5 %. The solution was defoamed, and while being maintained at 70° C., was extruded into a coagulating bath at a rate of 316 cc/min. through a doughnut-shaped spinneret having 34,000 holes each with a diameter of 0.07 and provided at one end of the spinning coagulating bath. While being coagulated in the form of filaments, the extrudate was taken up at a velocity of 2.50 m/min.

The distance between the spinneret face and the top surface of the coagulating bath was 85 cm. An aqueous inorganic acid salt solution of the composition indicated in the following table having an N-methyl-2-pyrrolidone concentration of 1.7 ± 0.2 % and a specific gravity at 60° C. of 1.398 was fed into the coagulating bath from the rear of the spinneret.

The coagulating liquid was caused to flow at an average velocity of 0.20 m/min. (the yarn take-up velocity × 0.08), and from the yarn take-up side of the coagulating bath, a coagulating liquid having an NMP concentration of 6.5 ± 0.5 % and a specific gravity at 60° C. of 1.372 was discharged.

| Composition of the coagulating liquid | | Temperature of the coagulating liquid |
|---|---|---|
| (1) | 35 % calcium chloride and 8 % magnesium chloride | 95° C. |
| (2) | 25 % calcium chloride and 18 % magnesium chloride | 95° C. |
| (3) | 35 % calcium chloride and 18 % calcium nitrate | 95° C. |
| (4) | 25 % calcium chloride and 18 % calcium nitrate | 60° C. |
| (5) | 25 % calcium chloride and 15 % zinc chloride | 60° C. |
| (6) | 25 % calcium chloride, 10 % zinc chloride and 5 % calcium nitrate | 75° C. |

The resulting undrawn tow was washed with water until the amount of the residual solvent in the fiber reached 8 %, and then drawn to 2.2 times the original length in hot water at 97° C. Subsequently, the two was dried over a hot roller, and heat-treated on a hot plate at 340° C. while imparting a 90 % stretch to the tow. The two was oiled, crimped and cut to make staple fibers.

On the other hand, the coagulating liquid discharged from the spinning cell was collected in a tank, and its temperature was adjusted to 50° C. Then, the coagulating liquid was fed into an extracting tower, where it was extracted with 1.5 times its volume of methylene chloride. The methylene chloride layer containing N-methyl-2-pyrrolidone was withdrawn from the upper part of the extracting tower, and evaporated and distilled to separate methylene chloride from N-methyl-2 pyrrolidone. The coagulating liquid after extraction was withdrawn from the lower part of the extracting tower, and recycled to the spinning process.

The resulting fibers had the following properties.

| Composition of the coagulating liquid | Denier | Tenacity (g/de) | Elongation (%) | Rate of tenacity fluctuation(%) |
|---|---|---|---|---|
| (1) | 2.03 | 5.29 | 36.0 | 8.3 |
| (2) | 2.05 | 4.97 | 34.1 | 7.6 |
| (3) | 2.03 | 5.33 | 33.0 | 6.5 |
| (4) | 2.04 | 5.07 | 30.2 | 12.6 |
| (5) | 2.00 | 5.18 | 32.4 | 10.8 |
| (6) | 2.02 | 5.54 | 34.0 | 8.6 |

EXAMPLE 12

A wholly aromatic polyamide having an inherent viscosity of 1.95 and obtained by copolymerizing 45 mol% of m-phenylene diamine, 45 mol% of isophthaloyl chloride and 10 mol% of m-aminobenzoyl chloride was dissolved in NMP to form a spinning solution having a polymer concentration of 20 %. The solution was extruded into a coagulating bath at a rate of 234 ml./min. through a spinneret having 6000 holes each with a diameter of 0.12 mm which was provided at one end of the coagulating bath, and coagulated therein in the form of filaments, followed by taking up at a rate of 2.1 m/min.

A coagulating liquid at 95° C. consisting of a 43 % aqueous solution of calcium chloride having an NMP concentration of 1.7 % was fed into the coagulating bath from the rear of the spinneret, and caused to flow in the coagulating bath at an average flow velocity of 0.17 m/min. A coagulating liquid having an NMP concentration of 6.0 % and a specific gravity at 60° C. of 1.382 was discharged from the yarn outlet of the coagulating bath.

The filaments which were withdrawn from the coagulating bath were thoroughly washed with water to remove the solvent, drawn to 2.76 times the original length in boiling water held at 95° C., dried, and then drawn to 1.60 times on a hot plate held at 300° C.

The spinning and drawing conditions were good, and there was not such trouble as the agglutinization, opacification or breaking of the filaments. The fibers obtained had a tenacity of 4.47 g/denier and an elongation of 30 %.

On the other hand, the coagulating liquid discharge from the coagulating bath was fed to a reservoir and its temperature was adjusted to 50° C. Then, it was fed into an extraction tower, where it was treated with 1.3 times its volume of methylene chloride to extract and recover NMP in the coagulating liquid. By this treatment, a calcium chloride aqueous solution having an NMP concentration of 1.7 % was continuously withdrawn from the extraction tower, and recycled to the coagulation bath.

What we claim is:

1. A process for producing wholly aromatic polyamide filaments having at least 75 mol% of the recurring units being derived from m-phenylene isophthalamide, said process comprising extruding a spinning solution of said wholly aromatic polyamide in an amide solvent having a polymer concentration of 15 to 30 % by weight and being free of inorganic salts through a spinneret into an aqueous coagulating bath containing a total concentration of calcium chloride, magnesium chloride, calcium nitrate and zinc chloride of at least 35% by weight of liquid and a concentration of calcium chloride of at least 20% by weight of liquid and having an amide solvent concentration of not more than 3% by weight of liquid to the vicinity of said spinneret, said amide solvent essentially consisting of N-methyl-2-pyrrolidone, taking-up the coagulated filaments from the lower portion to the upper portion of the coagulating bath, flowing the coagulating liquid in said bath at an average velocity from 0.04 to 0.1 times the velocity of filament take-up in the filament advancing direction, discharging the coagulating liquid having a specific gravity, measured at 60° C of at least 1.36 and an amide solvent concentration of not less than 4% by weight from said bath, extracting N-methyl-2-pyrrolidone from the discharged coagulating liquid with an organic solvent consisting essentially of methylene chloride, and recovering the N-methyl-2-pyrrolidene from the organic solvent.

2. The process of claim 1 wherein the spinneret has at least 5000 holes.

3. The process of claim 1 wherein said aqueous coagulating liquid is an aqueous solution of calcium chloride in a concentration of at least 35%.

4. The process of claim 1 wherein the temperature of the aqueous coagulating liquid is at least 60° C.

5. The process of claim 1 wherein the coagulating liquid from which a part or whole of the amide solvent has been removed by extraction with methylene chloride is recycled to the coagulating bath.

6. The process of claim 1 wherein the N-methyl-2-pyrrolidone solvent is recovered from the methylene chloride by evaporation and distillation, and is used in the preparation of the spinning solution.

* * * * *

UNITED STATES PATENT OFFICE
CERTIFICATE OF CORRECTION

Patent No. 4,073,837　　　　　　　　　Dated February 14, 1978

Inventor(s) Kouzai, et al.

It is certified that error appears in the above-identified patent and that said Letters Patent are hereby corrected as shown below:

Item [73], delete "Teitin", insert --Teijin--

Signed and Sealed this

Twenty-seventh Day of June 1978

[SEAL]

Attest:

RUTH C. MASON
*Attesting Officer*

DONALD W. BANNER
*Commissioner of Patents and Trademarks*